(12) United States Patent
Karapetyan

(10) Patent No.: US 6,800,088 B1
(45) Date of Patent: Oct. 5, 2004

(54) MULTICOMPARTMENT ICE BAG FOR SINGLE PATIENT USE

(76) Inventor: Armen Karapetyan, 1935 N. Van Ness Ave., Los Angeles, CA (US) 30068

( * ) Notice: Subject to any disclaimer, the term of this patent is extended or adjusted under 35 U.S.C. 154(b) by 0 days.

(21) Appl. No.: 10/420,683

(22) Filed: Apr. 21, 2003

(51) Int. Cl.$^7$ .................................................. A61F 7/00
(52) U.S. Cl. ........................................ 607/104; 607/96
(58) Field of Search .......................... 607/96, 108, 109, 607/110, 111, 112, 114, 104, 113

(56) References Cited

U.S. PATENT DOCUMENTS

| | | | |
|---|---|---|---|
| 3,995,621 A | * 12/1976 | Fletcher et al. | ............. 600/474 |
| 4,275,485 A | 6/1981 | Hutchison | |
| 4,347,848 A | 9/1982 | Hubbard et al. | |
| 4,523,353 A | 6/1985 | Hubbard et al. | |
| 5,846,446 A | 12/1998 | Jackson | |
| 6,322,044 B1 | 11/2001 | Vangedal-Nielsen | |

* cited by examiner

*Primary Examiner*—Roy D. Gibson
*Assistant Examiner*—Aaron Roane

(57) ABSTRACT

A multicompartment ice bag for single patient use provides a possibility to apply a cold to a small areas of the single patient body. An improved multicompartment ice bag for single patient use includes a multicompartment bag, comprising at least two of a plurality of compartments, each of which includes at least one of a plurality of compartment openings for fluid passage into compartments, an inlet opening for fluid passage into the bag, at least two of strings, one of which is solid and another one is of hollow configuration providing a channel for fluid passage into the bag, and a squeezing proving outside closing of the compartment openings at the time of fluid freezing process.

3 Claims, 6 Drawing Sheets

MULTICOMPARTMENT ICE BAG FOR SINGLE PATIENT USE

FIELD OF THE INVENTION

This invention is generally related to an ice bag and more particularly to ice bag containing a frozen liquid (preferably water) intended for medical patient use to cold a small areas of the patient body.

BACKGROUND OF THE INVENTION

The ice bags are in wide use. Ice cubes mostly have been molded in trays which are filled with water an placed in a freezing equipment. For example, the ice packs for single patient use are generally of two types: large general purpose ice packs designed for application to large areas of the body and small, specialized ice packs designed for application of cold locally at particular points. These smaller ice packs, because of their size, typically have small openings, which are difficult to fill from an automatic ice machine or from a scoop from an ice bin, and which often result in the spillage of ice during filling and damage to the disposable ice packs which tend to be of more fragile construction. Sanitation requirements also limit the use of the ice packs in hospitals and clinics. Many small ice packs, for example, designed for single patient use, must be disposed of after single use due to the likelihood of contamination of the ice machine or scoop with an ice pack which has been in contact with a patient's body, or there is risk of contaminating the ice supply. This is both expensive and wasteful. The U.S. Pat. Nos. 4,347,848 and 4,523,353 describe a single patient ice pack which can be filled and refilled from an automatic ice machine and includes the singular ice pack of a rectangular envelope form having two sides, an open, a closed end, and two pairs of tie strings and extend from the open and closed ends. A bag closed on three sides and having a throat opening at the open end of the envelope is formed internally of the envelope for receiving and retaining ice. A funnel dimensioned to conform with the divergence of the throat in the bag may be inserted into the throat for filling the bag by ice from the automatic ice machine. A closure member is provided for sealing the throat of the bag when the bag has been filled with ice.

Such ice bag can be uncomfortable for patients considering the sharp corners of the ice cubes filled by automatic ice machine.

For some reasons, after the ice cubes have been molded in trays which are filled with water and frozen in a freezing equipment, it can be necessarily to remove the piece of ice from the bag. A release mechanism permits the ice cubes to be removed intact for use. The two primary release means, a lever moving baffles and the flexible tray after result in the ice cubes breaking. This method has been improved upon by a mold bag with shapes molded in. The mold bag is filled with liquid and placed in a freezing equipment. Removal of the ice cubes is accomplished by tearing the mold bag to release the ice pieces. A problem with the mold bag is that air can enter during any part of the process which causes less ice to be formed and in some cases cosmetic flaws in the resulting ice cubes. The risk of air entry is especially high during the process of sealing the bag. What is desired is a mold bag which can be sealed without permitting the entry of air. This requires a seal on the filling end of the bag it is further desirable that the sealing be automatic. For example, the U.S. Pat. No. 5,846,446 describes an ice making bag comprising a first left peripheral opening binding and a first right peripheral opening binding. The first left peripheral opening binding and the first right peripheral opening binding form a gap therebetween. The first binding functions to form a pocket between the first envelope top and the first envelope bottom. The first ice making bag also includes one first opening binding forming an air channel between the first left peripheral opening binding or the first right peripheral opening binding and another first opening binding. A user holds the first ice making bag in a vertical position pouring liquid in through the gap into the pocket formed between the first envelope top, and a first envelope bottom and placing the first ice making bag in a freezer to form first ice. The air channel functions to facilitate release of air previously entrapped in the pocket during filing.

This ice making bag is complex and requires automatic nozzle sealing under pressure.

It is commonly known within this technical field that ice cube bags with very strong joints, especially weldings or glueings may be produced, providing a safe and reliable containment of the ice cubes produced by means of the ice cube bag. Similarly it is generally realized that it may often be quite difficult for a user to open an ice cube bag in which ice cubes are contained, as the foil used, especially the commonly used polyethylene plastic foil and the rather strong joints, makes a tearing apart or opening of the ice cube bag quite difficult. In some known ice cube bags, an ice cube bag construction is described in which glueing is preferably used for establishing joints in the interior of the ice cube bag. The joints are later on relatively easy to separate again enabling a conversion of the ice cube bag from an ice cube bag divided into compartments into a non-compartmentalized ice cube bag and the joints enabling a conversion of the ice cube bag from a compartmentalized ice cube bag into a non-compartmentalized ice cube bag may be established as weldings or alternatively as glueings, as it should be possible for a person skilled in the art to deduce a technique to establish weak weldings enabling such a tearing apart of the joints for the purpose of converting the ice cube bag from a compartmentalized into a non-compartmentalized form. In this connection, tearing apart of the joints, especially the glueings is not to cause any damage to the walls of the ice cube bag, i.e. cause a proper tearing of the ice cube bag, but only a separation of the joints previously established. The U.S. Pat. No. 6,322,044 describes an ice cube bag comprising two sheet-shaped foil layers defining an outer periphery. A peripheral joint extends along the major part of the outer periphery of the foil layers, with the exception of a peripheral area constituting an inlet aperture of the bag. Their peripheral joint joins the foil layers together defining an inner chamber which is divided into several ice cube sections defined by separate joints of the foil layers. An inlet channel extends from the inlet aperture to the inner chamber of the bag providing admission from the surroundings to the inner chamber of the bag through the inlet channel. Each of the separate joints is constituted by a number of individual joints, each of these individual joints establishing a connection between the two sheet-shaped foil layers with such a joint strength and with such a limited area extension that the individual joint is not broken when the foil layers are exposed to a separation force, but provides a tearing apart or perforation in one of the foil layers along the periphery of the individual joints.

Such ice cube bag requires each of the foils to have a folded part and protruding inwardly into the interior of the ice cube bag and forming inner laid-open edges.

There are many disclosures of sealing devices designed for a wide variety of purposes and having many different constructions. In some devices, resilient clips are provided including portions resiliently movable apart to receive a portion of a bag or other enclosure therebetween. In others, the devices have been arranged to be deformed to clamp portions of a bag or the like between portions of the devices. The sealing device by U.S. Pat. No. 4,275,485 includes two members connected through a hinge for clamping and sealing engagement with gathered-together material at the end of an enclosure. The hinge facilitates installation and accurately aligns interacting parts including a projecting structure on one member with an opening in the other, interengageable locking elements on side portions of the members and sealing elements on end portions of the members. The locking elements include a shoulder on one member engageable by a shoulder on a projection on the other, the projection being engageable in one embodiment for release. Additional locking elements are positioned adjacent the hinge connection for reinforcement.

The described sealing device is complex and requires the hinge, which facilitates installation and aligns interacting parts.

Thus, there is a great need in the art for the improved ice bag, providing convenient, economical, effective and safe use for single patient.

OBJECT AND ADVANTAGES OF THE INVENTION

Accordingly, several objects and advantages of the present invention are to provide convenient, economical and effective ice bag for single patient use in the application of cold to small areas of the body.

It is another object of the invention to eliminate necessity of the automatic ice machine use.

It is still another object of the invention to provide patient with possibility to use the improved ice bags in the residence and not only in the medical clinics provided with the automatic ice machines.

It is further object of the invention to increase the a flexibility of the patient's ice bags and to prevent the damage to the ice bag material at the time of the folding of the bag with the frozen liquid (ice) inside.

It is still further object of the invention to eliminate the patient inconvenience of the application of sharp sides of the ice cubes formed by the automatic ice machines.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

In view of the foregoing disadvantages inherent in the known prior art, the present invention provides a new single patient multicompartment ice bag to apply a cold to a small areas of the patient body. As such, the general purpose of the present invention, which will be described hereinafter in greater details, is to provide a new convenient, economical and effective individual multicompartment ice bag for patient treatment. The improved multicompartment ice bag has many of the advantages of the medical ice packs mentioned heretofore and many novel features that result in the convenience and safety of personal use, which is not anticipated, rendered obvious, suggested or even implied by any of prior art ice bags for single patients. For example, the single patient ice bag with compartments is more flexible, than the ice bag without compartments, and the surface of the multicompartment ice bag filled in by fluid (preferably water) is smooth and does not have the sharp angles intrinsic in the patient ice bag filled by the ice cubes.

To attain this, the present invention generally includes a multicompartment bag, comprising at least one of a plurality of compartments, each of which includes at least two of a plurality of compartment openings for fluid passage into compartments, an inlet opening for fluid passage into the bag, at least two of strings, one of which is solid and another one is of hollow configuration providing a channel for fluid passage into the bag, and a squeezing means providing outside closing of the compartment openings at the time of fluid freezing process.

DESCRIPTION OF THE PREFERRED EMBODIMENTS

Here the description of an improved multicompartment ice bag for single patient use will be done in statics (as if the components of the improved apparatus are suspended in the space) with description of their relative connections to each other. The description of the functional operations will be done hereinafter.

Figure 1:
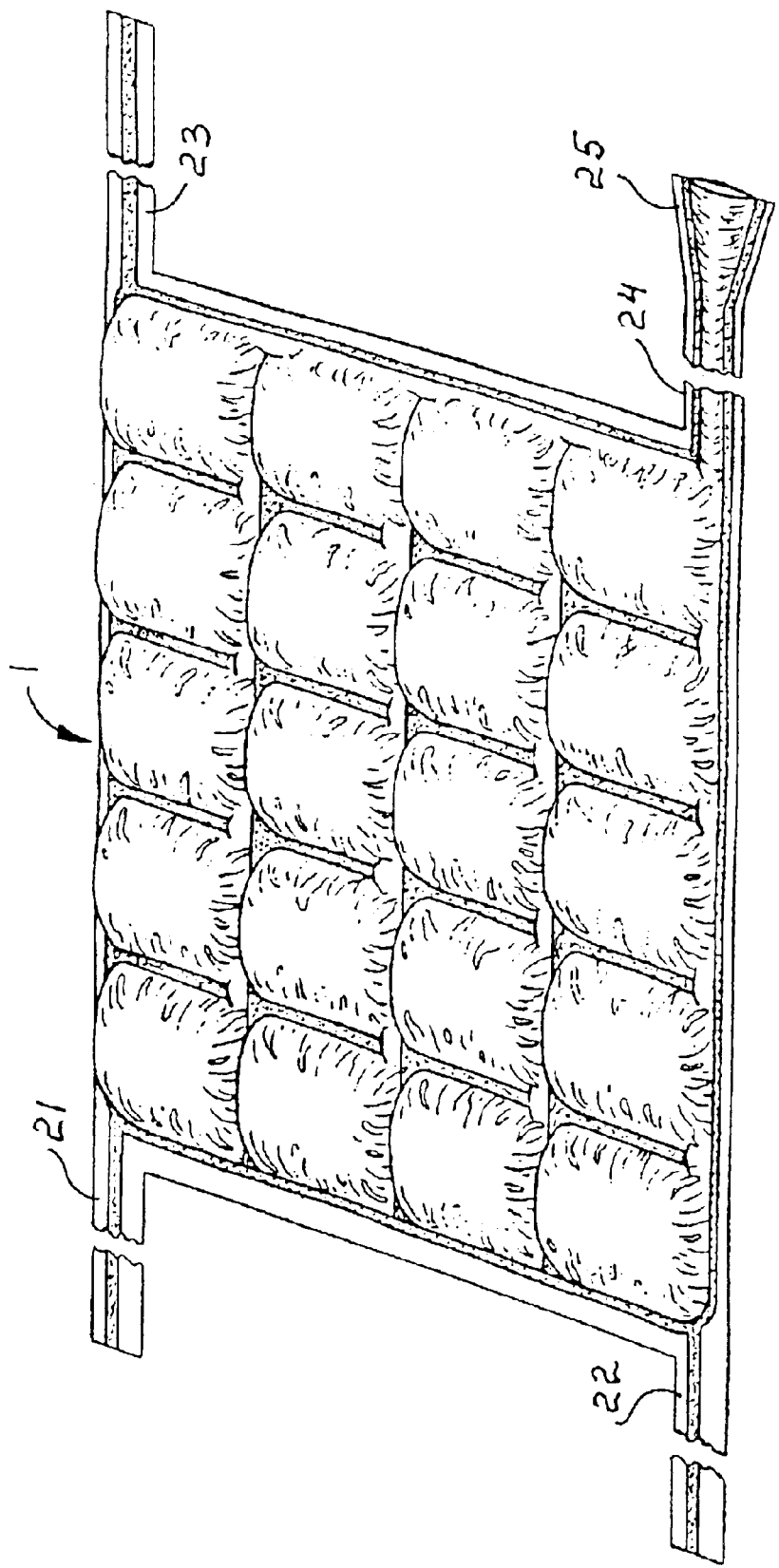
FIG. 1 is a simplified spatial view of an improved multicompartment ice bag for single patient use.
Figure 2:
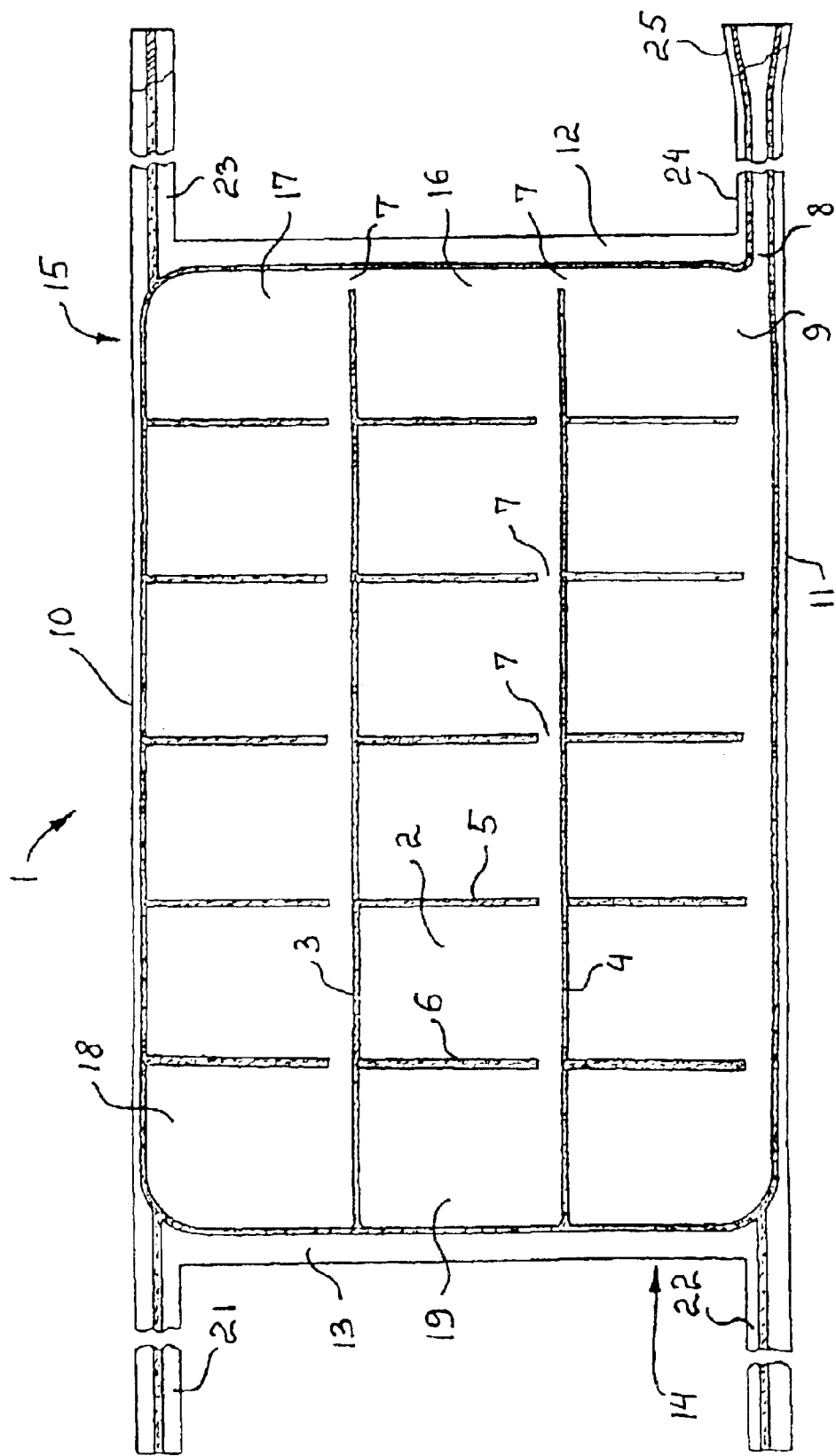
FIG. 2 is a simplified drawing of a multicompartment ice bag.
Figure 3A:
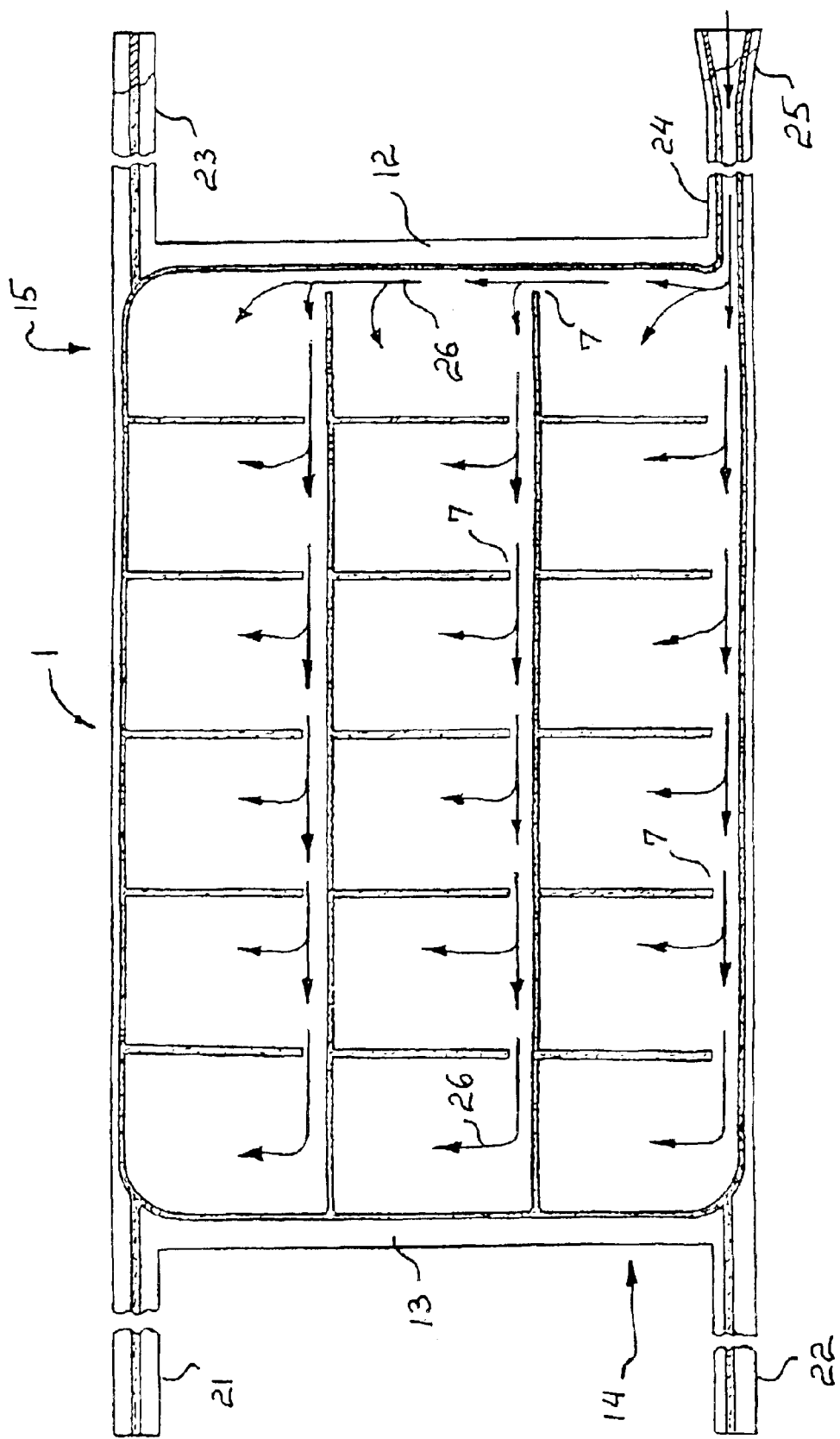
FIGS. 3a, 3b are the simplified illustrations of fluid flow, filling an improved multicompartment ice bag
Figure 3B:
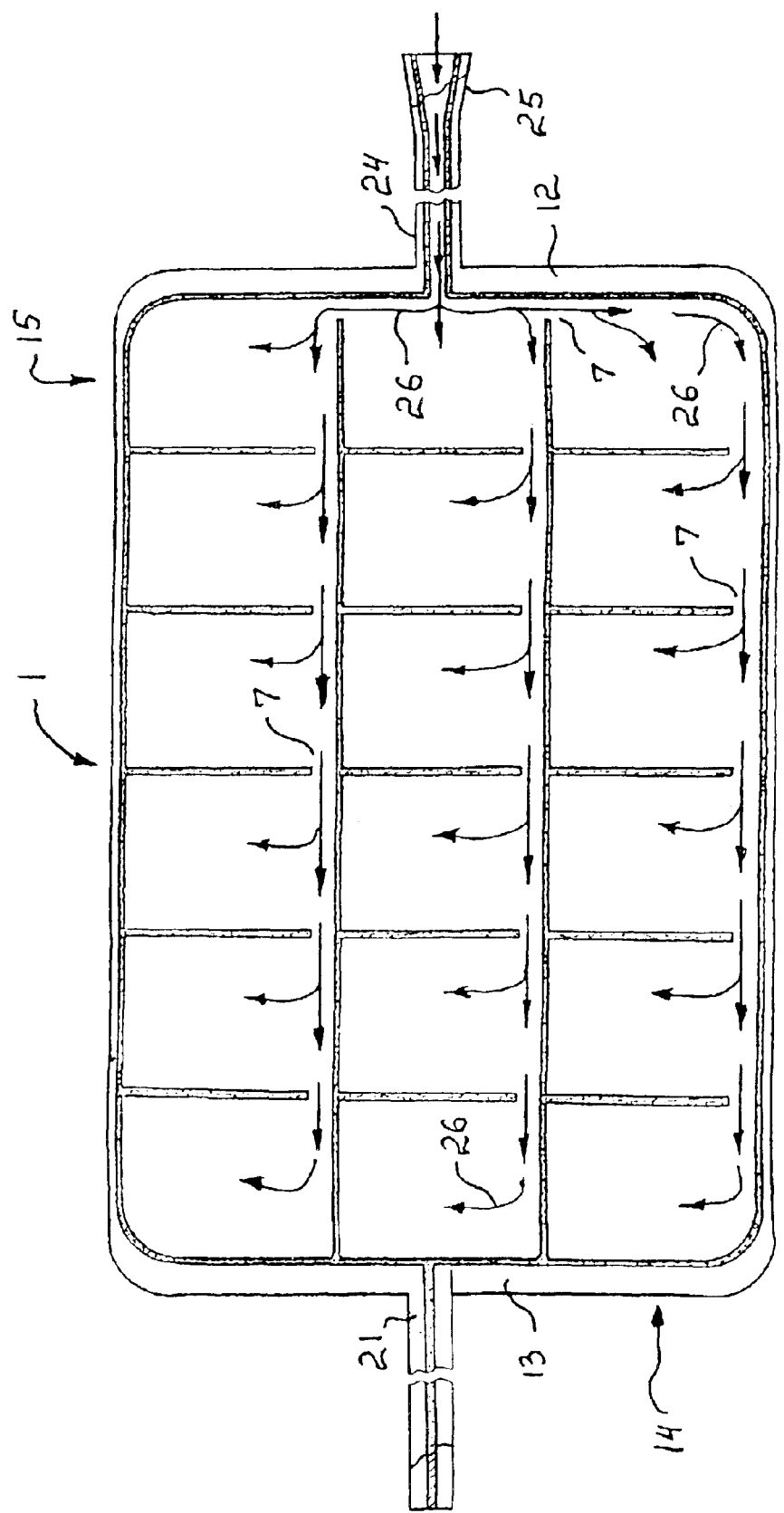
Figure 4:
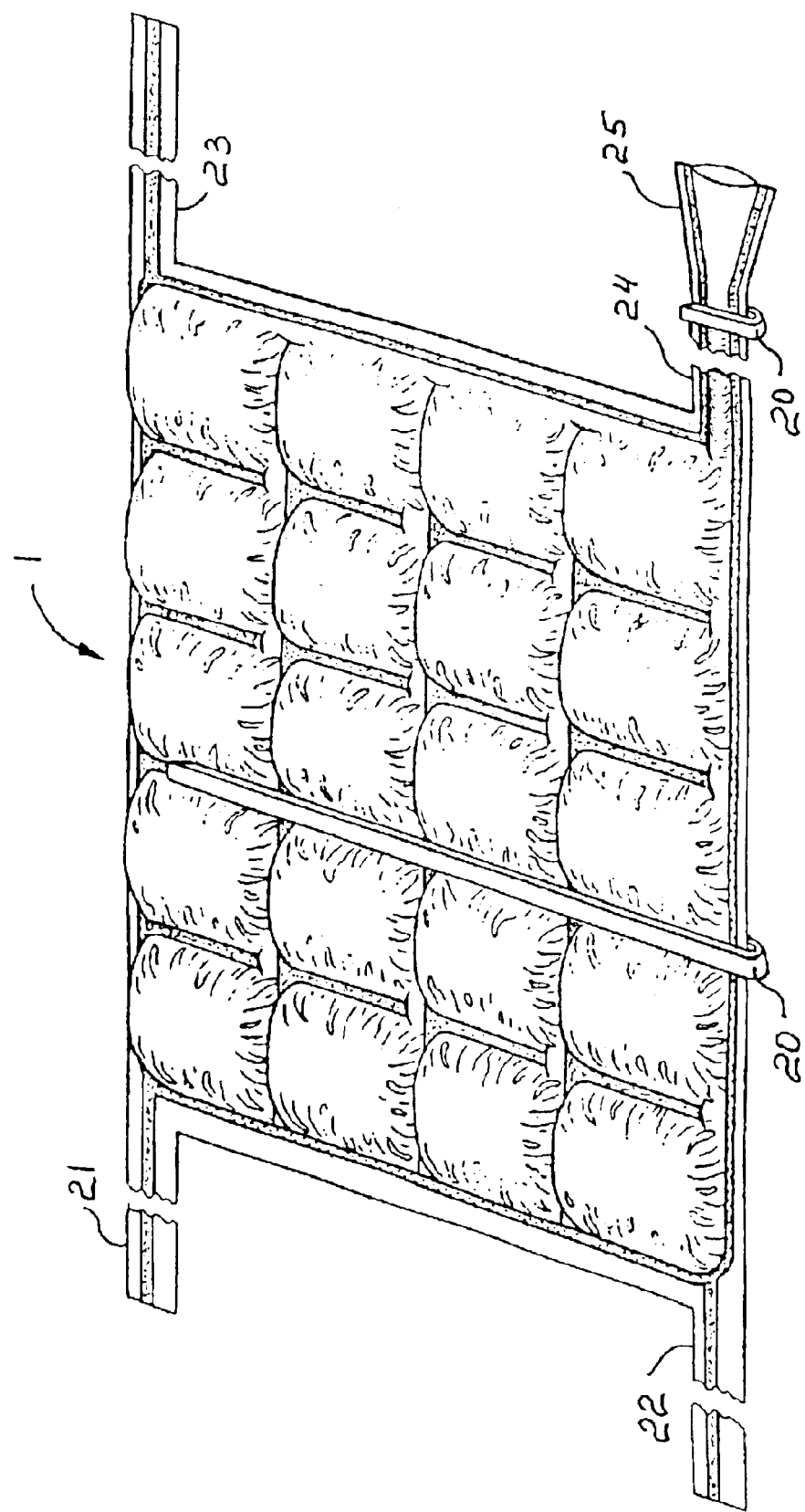
FIG. 4 is a simplified illustration of a squeezing means use.

An improved multicompartment ice bag for single patient use includes a multicompartment ice bag 1, shown on FIGS. 1–5. The multicompartment ice bag 1 can be of any convenient geometrical form/configuration. In FIGS. 1–5 is conventionally shown that the multicompartment ice bag of rectangular form. The multicompartment ice bag 1, having the first side 10 and second side 11, the inlet side 12 and a closed end 13, includes at least two of a plurality "N" (where N=2, . . . , i, . . . , n–1, n) of compartments and an inlet opening 8 coupled with the first compartment 9. The bag 1 includes at least one of a plurality "M" (where L=1, 2, . . . ,j, . . . , m–1, m) of compartment rows, and at least one of a plurality "H" (where H=1, 2, . . . , h–1, h) of compartment columns. In FIGS. 1, 4 it is conventionally shown the multicompartment ice bag 1 with four rows (m=4) and five columns (h=5), and the first row 14 is shown at the bottom of the bag 1 and the first column 15 is shown on the right side of the bag 1. FIGS. 2, 3a, 3b illustrate the multicompartment ice bag 1 including conventionally three rows (m=3) and six column (h=6). Each compartment comprises at least one compartment opening 7 in FIG. 2 it is conventionally shown single compartment opening 7 for each compartment, for example, an i-th compartment 2 and an adjacent (n–1)-th compartment 19 include the opening 7 on their right sides respectively). Each middle adjacent compartment (for example, i-th compartment 2) is closed on its first side 3 and second side 4, and includes an opening 7 on the other two sides first open side 5 and second open side 6 respectively. The second compartment 16 has only one closed side and includes three openings 7. The first compartment 9 has only one closed side and includes two openings 7 and an inlet opening 8. The inlet opening 8 provides the passage of the fluid (preferably water) into bag 1. The closed side 13 of the multicompartment ice bag 1 can include at least one string (first string 21), and the inlet side 12 of the multicompartment ice bag 1 can include an appropriate at least one string (inlet string 24) respectively, as shown in FIG. 3b. In FIGS. 1–3a it is conventionally shown the bag 1 with four strings 21–24. The first string 21 is extended from a closed side 13 along the first side 10, and the second string 22 is extended of the closed side 13 along the second side 11. The inlet side 12 includes the third 23 and inlet 24 strings likewise extended from the inlet side 12 along the first side 10 and second side 11 respectively. The first 21 and second 22 strings are parallel to each other, and the pair of strings 23 and 24 are parallel to each other too. The first 21, second 22 and third 23 strings are solid and preferably of the flat configuration. The inlet string 24 is hollow (is formed as a tube) in order to provide the fluid passage through the mentioned inlet string 24 via inlet opening 8 into bag 1. The first compartment 9 is coupled with the inlet string 24. The inlet string 24 can have a slightly conic configuration at its end 25, as shown in FIGS. 1–4, in order to provide the convenient fluid filling, for example, from sink's faucet (not shown). The strings can be attached/connected (not shown) to the ice bag 1 instead of to be extended from the ice bag 1 material, as shown in FIGS. 1–4. The multicompartment ice bag 1 can be produced of any flexible, slightly stretchable material, such as plastic, polyethylene, etc. The multicompartment ice bag 1 can, for example, be manufactured of two sheets of material welded or glued along the perimeter o f the bag 1 and between adjacent compartments. The spaces between adjacent compartment closed sides are welded or glued with no any openings, and the spaces between adjacent compartments open sides, having the compartment opening, are welded or glued with the appropriate openings, providing fluid flow passage from one compartment to another adjacent compartment of the bag 1.

The multicompartment ice bag 1 employed for single patient use in the application of cold to small areas of the body also comprising a squeezing means 20. The squeezing means 20, shown in. FIG. 4, is a clipping/squeezing means intended for outside closing of the compartment openings 7 after the multicompartment ice bag 1 is filled in with a fluid and before the bag 1 is placed for freezing. Without squeezing means 20, the frozen fluid (ice) will be presented in the compartment openings 7, and at the time of the folding of the bag 1 around the area of the patient body to be cold, the broken piece of ice inside the compartment opening can have the sharp edge of the broken cross-section, which can damage the material (for example, to tear the material) of the bag 1. The squeezing means 20 prevents the forming of the ice inside the compartment openings 7 during fluid freezing process. Also, the squeezing means 20 can be used for the reverse fluid leakage prevention during fluid freezing process by closing (squeezing) fluid passage inside inlet string 24, as shown in FIG. 4.

Figure 5:
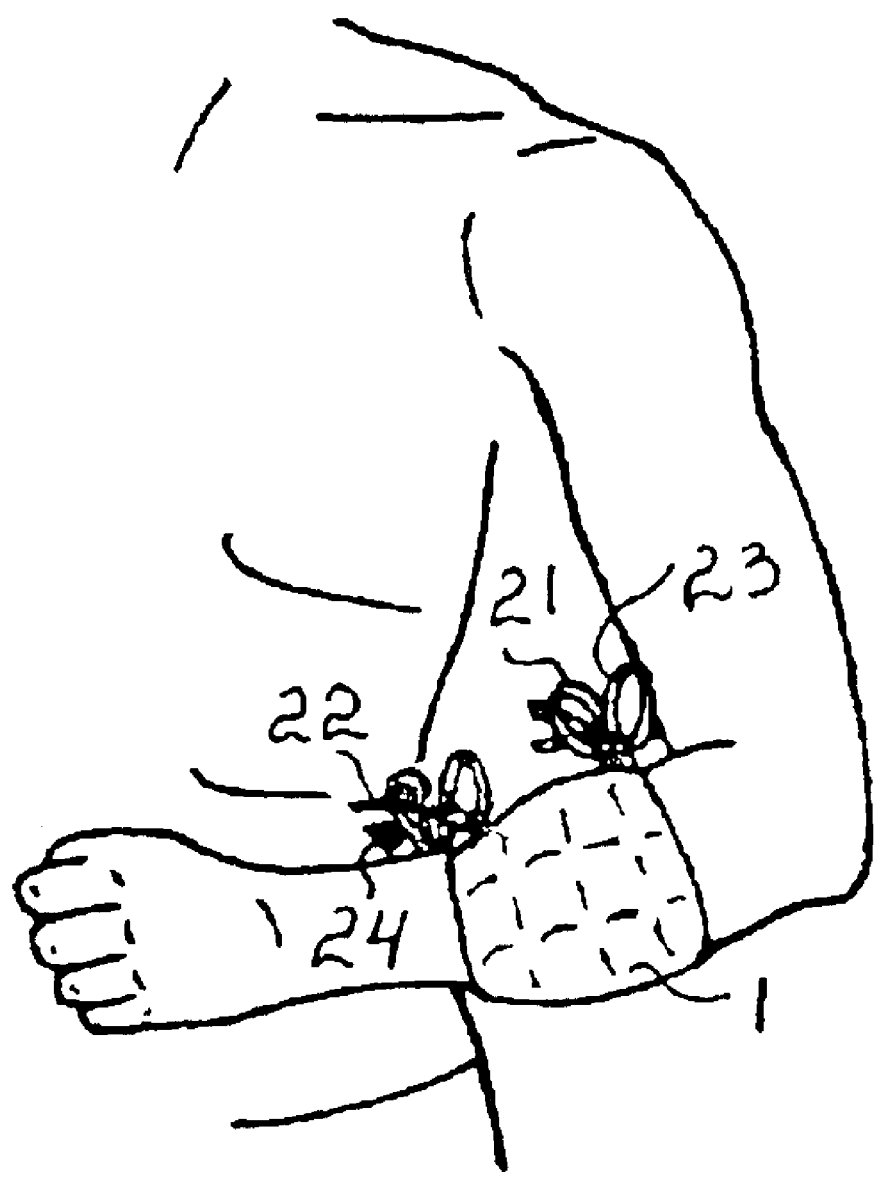
FIG. 5 is a simplified illustration of the improved ice bag application to the small area of the patient body to be cold.

The improved multicompartment ice bag 1 for single patient use operates as follows below. Initially, the multicompartment ice bag 1 is empty. The conic end 25 of the inlet string 24 is coupled, for example, with the sink's faucet (not shown) and the fluid is filled into compartments of the bag 1 through the inlet opening 8 and compartment openings 7, as shown in. FIGS. 3a, 3b, where the fluid flow 26 is presented by errows. Preferably, the bag 1 should not be fully filled in, considering freezing water expansion. After the water is filled in, the squeezing means 20 is installed over the inlet string 24 (see illustration in FIG. 4) squeezing the string 24, thereby eliminating the fluid reverse leakage. Also, the squeezing means 20 are installed in appropriate manner onto the bag 1 to close all compartment openings 7 of the bag 1. After that, the bag 1 can be placed into freezer. When the fluid is frozen, all squeezing means 20 from compartment openings are removed, and the bag 1 can be folded around patient body area to be cold. The prevention of the fluid reverse leakage through the passage into inlet string 24 can be provided, for instance, by the knot on the string 24, or by the use of the squeezing means 20 or any other clipping devices, providing non-leaking clipping/squeezing of the string 24. The strings 21 and 23, and strings 22 and 24 are coupled in pairs respectively. The strings coupling can be provided by knots, as shown in FIG. 5, or using the squeezing means 20, clipping devices or any other coupling devices, such as "Velcro", providing sufficiently reliable connection.

Thus, an improved multicompartment ice bag provides convenient, economical and effective use ice pack by single patient without necessity to use automatic ice machine.

CONCLUSION, RAMIFICATION AND SCOPE

Accordingly the reader will see that, according to the invention, I have provided a multicompartment ice bag for single patient use, providing convenient, economical and effective single patient ice bag intended for application of cold to small areas of the patient body. An improved multicompartment ice bag for single patient use has various possibilities, considering activities of the patient treatments.

While the above description contains many specificities, these should be not construed as limitations on the scope of the invention, but as exemplification of the presently-preferred embodiments thereof Many other ramifications are possible within the teaching to the invention. For example, an improved multicompartment ice bag for single patient use eliminates the necessity of the automatic ice machine, providing possibility to use the improved ice bag not only in medical offices and clinics, but also at home, children care centers, retired houses, etc. for single patient use more time for them to use for patients. Also, an improved ice bag is not disposable after single use and can be used repeatedly.

Thus, the scope of the invention should be determined by the appended claims and their legal equivalents, and not by examples given.

THE DRAWING REFERENCE NUMERALS WORKSHEET

1.—a multi compartment ice bag;
2.—an i-th compartment;
3.—a first compartment closed side;
4.—a second compartment closed side,
5.—a first compartment open side;
6.—a n-th compartment open side;
7.—an opening;
8.—an inlet opening;
9.—a first compartment;
10.—a first side of the ice bag 1,
11.—a second side of the ice bag 1;
12.—an inlet side of the ice bag 1;
13.—a closed side of the ice bag 1;
14.—a first row of compartments;
15.—a first column of compartments;
16.—a second compartment;
17.—a third compartment;
18.—a n-th compartment;
19.—a (n-l)-th compartment;

20.—a squeezing means;
21.—a first strings;
22.—a second string;
23.—a third string;
24.—an inlet string;
25.—a conic free end of the inlet string 24;
26.—a fluid flow.

What is claimed is:

1. A multicompartment ice bag for single patient use comprising
   at least two of a plurality of compartments, each of which comprises at least one of a plurality of compartment openings for a passage of a fluid into said compartments of said multicompartment ice bag;
   an inlet opening for fluid passage into said multicompartment ice bag;
   at least two of a plurality of strings, wherein a first string is extended from a closed side of said multicompartment ice bag and is of a solid configuration, and a second string is extended from an inlet side of said multicompartment ice bag and is of hollow configuration, providing a channel for the passage of said fluid into said multicompartment ice bag, and wherein said second string is extended of said inlet side of said multicompartment ice bag at the place of a location of said inlet opening, wherein the channel of the second string is closed offer the multicompartment ice bag filled with fluid.

2. The ice bag of claim 1, wherein said second string further includes a conic form free end.

3. The ice bag of claim 1, wherein said first string is further connected to said closed side of said multicompartment ice bag, and said second string is further connected to said inlet side of said multicompartment ice bag, and wherein the connection of said second string with said inlet side is located at the place of said inlet opening.

* * * * *